US012799047B2

(12) United States Patent
Kobayashi

(10) Patent No.: US 12,799,047 B2
(45) Date of Patent: Nov. 17, 2026

(54) METHOD FOR PRODUCING ALPHA-OLEFIN

(71) Applicant: IDEMITSU KOSAN CO., LTD., Tokyo (JP)

(72) Inventor: Ryoichi Kobayashi, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 547 days.

(21) Appl. No.: 18/562,433

(22) PCT Filed: May 2, 2022

(86) PCT No.: PCT/JP2022/019509
§ 371 (c)(1),
(2) Date: Nov. 20, 2023

(87) PCT Pub. No.: WO2022/255024
PCT Pub. Date: Dec. 8, 2022

(65) Prior Publication Data

US 2024/0239727 A1 Jul. 18, 2024

(30) Foreign Application Priority Data

Jun. 3, 2021 (JP) ................................ 2021-093786

(51) Int. Cl.
*C08F 10/02* (2006.01)
*C07C 2/04* (2006.01)
(Continued)

(52) U.S. Cl.
CPC ................ *C07C 2/406* (2013.01); *C07C 2/04* (2013.01); *C08F 6/02* (2013.01); *C08F 10/02* (2013.01);
(Continued)

(58) Field of Classification Search
CPC ...... C08F 6/02; C08F 6/06; C08F 2/01; C08F 10/02; C07C 2/04; C07C 2/06; C07C 2/22
See application file for complete search history.

(56) References Cited

U.S. PATENT DOCUMENTS 3,857,795 A * 12/1974 Van Der Bend ........ C08F 10/00 502/103
10,221,109 B2 * 3/2019 Toda ..................... C08F 210/16
(Continued)

FOREIGN PATENT DOCUMENTS

EP 0444505 A2 * 9/1991 ............... C07C 2/32
EP 0444505 B1 * 9/1991 ............... C07C 2/32
(Continued)

OTHER PUBLICATIONS

Japanese Office Action issued on Nov. 11, 2025 in Japanese Patent Application No. 2023-525673 (with unedited computer-generated English translation), 11 pages.
(Continued)

*Primary Examiner* — Rip A Lee
(74) *Attorney, Agent, or Firm* — Oblon, McClelland, Maier & Neustadt, L.L.P.

(57) ABSTRACT

A method for producing an α-olefin may include (1) continuously introducing an ethylene and a catalyst into a reactor, followed by performing a polymerization reaction to obtain a reaction mixture; and (2) continuously introducing the reaction mixture and a base into a line mixer, followed by performing mixing. The line mixer may have a stirring power in a range of from 30 to 1000 kW·sec/$m^3$ and a number of passes may be in a range of from 5 to 50.

5 Claims, 1 Drawing Sheet

(51) Int. Cl.

| | |
|---|---|
| ***C07C 2/40*** | (2006.01) |
| ***C08F 2/01*** | (2006.01) |
| ***C08F 6/02*** | (2006.01) |
| *C07C 2/22* | (2006.01) |
| *C08F 6/06* | (2006.01) |

(52) U.S. Cl.

CPC .......... *C07C 2/22* (2013.01); *C07C 2527/135* (2013.01); *C07C 2531/14* (2013.01); *C08F 2/01* (2013.01); *C08F 6/06* (2013.01)

(56) References Cited

U.S. PATENT DOCUMENTS

| | | | | |
|---|---|---|---|---|
| 10,435,335 | B2 * | 10/2019 | Emoto | C07C 2/32 |
| 2003/0027947 | A1 | 2/2003 | Kobayashi et al. | |
| 2003/0153798 | A1 * | 8/2003 | Kobayashi | C07C 11/02<br>585/521 |
| 2018/0179122 | A1 | 6/2018 | Boutrot et al. | |
| 2019/0328629 | A1 | 10/2019 | Kitagawa et al. | |
| 2020/0055798 | A1 | 2/2020 | Miyamoto et al. | |

FOREIGN PATENT DOCUMENTS

| | | | | |
|---|---|---|---|---|
| JP | 3-220135 | A | | 9/1991 |
| JP | 7-216739 | A | | 8/1995 |
| JP | 10-7593 | A | | 1/1998 |
| JP | 2003-252829 | A | | 9/2003 |
| JP | 2015074617 | A | * | 4/2015 |
| JP | 5793899 | B2 | * | 10/2015 |
| JP | 2018-108983 | A | | 7/2018 |
| JP | 2021-62372 | A | | 4/2021 |
| WO | WO 2002/051777 | A1 | | 7/2002 |
| WO | WO 02/068365 | A1 | | 9/2002 |
| WO | WO 2018/092803 | A1 | | 5/2018 |

OTHER PUBLICATIONS

International Search Report and Written Opinion issued Jul. 19, 2022, in PCT/JP2022/019509 (with English Translation), 14 pages.

Japanese Office Action issued Jun. 24, 2025, in corresponding Japanese Patent Application No. 2023-525673 (with English Translation), 10 pages.

* cited by examiner

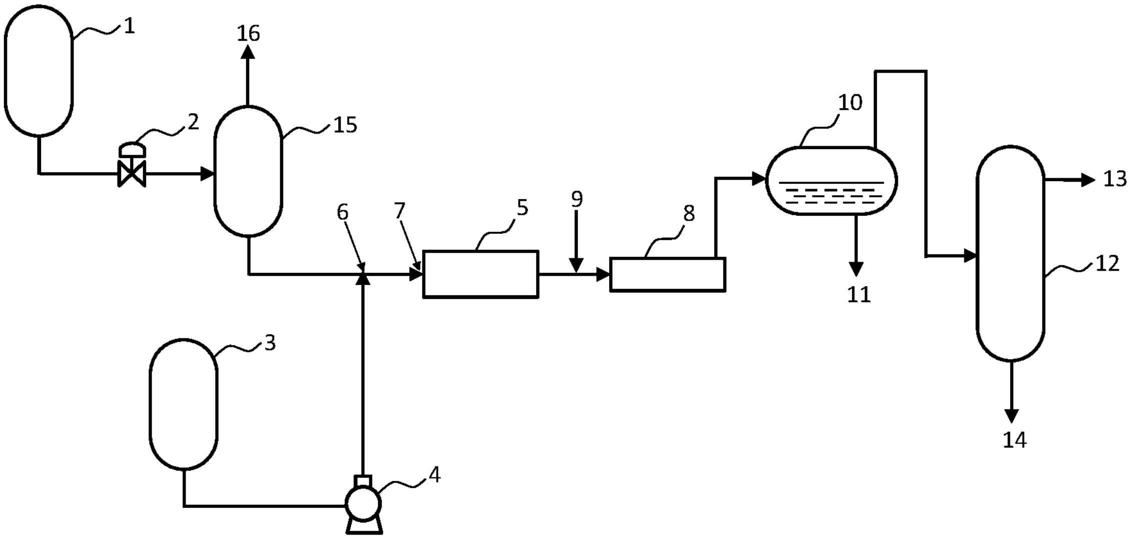
1
2
16
15
6
7
5
9
8
10
11
13
12
14
3
4

METHOD FOR PRODUCING ALPHA-OLEFIN

CROSS-REFERENCE TO RELATED APPLICATIONS

The present application is the national stage of international application PCT/JP2022/019509, filed on May 2, 2022, and claims the benefit of the filing date of Japanese Appl. No. 2021-093786, filed on Jun. 3, 2021.

TECHNICAL FIELD

The present invention relates to a method for producing an α-olefin.

BACKGROUND ART

α-Olefin is a useful substance widely used as a starting monomer material for olefin polymers, as a comonomer for a variety of high molecular polymers, and also as a starting material for plasticizers, surfactants, and the like.

α-Olefin has been intensively studied for its production methods. In general, for example, ethylene (having 2 carbon atoms) is oligomerized using a Ziegler-based catalyst to obtain a mixture of α-olefins having 4 to 20 carbon atoms such as butene (having 4 carbon atoms), hexene (having 6 carbon atoms), and octene (having 8 carbon atoms), or α-olefins having 20 or more carbon atoms, then, distillation is performed using plural distillation columns to isolate each of the α-olefins in the order of the number of carbon atoms such that components with smaller numbers of carbon atoms are first isolated, and each of the α-olefins or a mixture of α-olefins required for each of the applications is obtained.

The production process generally includes a polymerization-reaction step, a recovery step of unreacted ethylene, a deactivation step of catalyst, a deashing step, and a distillation step of solvent and α-olefin. Since the Ziegler-based catalyst and the like generally used in the above-described production process contain a halogen atom (halide ion) in the catalyst, hydrogen halide is generated by a reaction between the catalyst and water during a deactivation of the catalyst, and the hydrogen halide reacts with a hydrocarbon compound in a reaction mixture, thereby generating an organohalogen compound as a by-product. Therefore, attempts have been made to reduce such a by-product.

For example, PTL 1 discloses, for a purpose of stable operation without troubles such as clogging, and inhibition of by-production of organohalogen compounds, a method including polymerizing ethylene in the presence of a Ziegler-based catalyst, maintaining the liquid reaction product after the polymerization reaction at a temperature of 90° C. or more, and setting the pressure to be 3 kg/cm$^2$·G or more and introducing a basic nitrogen compound in an amount of 30 times by mol or more relative to the halogen content of the Ziegler-based catalyst, in a form of solution having a concentration of the basic nitrogen compound of 10% by weight or more, to deactivate the catalyst.

CITATION LIST

Patent Literature

PTL 1: JP 3-220135 A

SUMMARY OF INVENTION

Technical Problem

In a production of α-olefin, in order to deactivate catalyst while inhibiting organohalogen compounds as by-products, a stirring tank may be used. In order to inhibit a side reaction, it is necessary to rapidly deactivate catalyst and dilute the catalyst in water, and therefore a reaction mixture containing the catalyst and the α-olefin as the product needs to be introduced into a large amount of water and a large amount of basic substance. However, this is unsuitable for a continuous production since the facility becomes large and expensive relative to the production amount of the α-olefin. On the other hand, when the catalyst is deactivated without using a large amount of water and basic substance for enabling a continuous production, inhibition of by-production of the organohalogen compounds is difficult. Therefore, a facility and a method being suitable for a continuous production, being small but able to perform deactivation at high speed, and also being able to inhibit production of organohalogen compounds have been desired.

Accordingly, an object of the present invention is to provide a method for producing an α-olefin, which can deactivate catalyst in polymerization reactant efficiently, and inhibit by-production of organohalogen compounds.

Solution to Problem

In view of such circumstances, the present inventor has intensively studied and as a result, has found out that the above-described problems can be solved by a production method including a step of continuously introducing a reaction mixture of a polymerization reaction and a base into a line mixer, followed by performing mixing, to deactivate a catalyst, while setting an operation condition of the line mixer to fall within a specific range.

More specifically, the present invention relates to the following [1] to [5].

[1] A method for producing an α-olefin, including a step 1 of continuously introducing an ethylene and a catalyst into a reactor, followed by performing a polymerization reaction to obtain a reaction mixture, and a step 2 of continuously introducing the reaction mixture and a base into a line mixer, followed by performing mixing, in which in the mixing, a stirring power is 30 to 1000 kW·sec/m$^3$ and a number of passes is 5 to 50.

[2] The method for producing an α-olefin according to the above [1], including a step of bringing the reaction mixture into contact with the base before continuously introducing the reaction mixture and the base into the line mixer, in which a distance between a junction at which the reaction mixture contacts the base and an inlet of the line mixer is 1 m or less.

[3] The method for producing an α-olefin according to the above [1] or [2], in which the catalyst is a Ziegler-based catalyst.

[4] The method for producing an α-olefin according to any one of the above [1] to [3], in which the base is an ammonia.

[5] The method for producing an α-olefin according to any one of the above [1] to [4], further including, after the step 2, a deashing step 3 of removing the deactivated catalyst, and a distillation step 4 of recovering the α-olefin.

Advantageous Effects of Invention

According to the method for producing an α-olefin of the present invention, catalyst in polymerization reactant can be deactivated efficiently, by-production of organohalogen compounds can be inhibited, and α-olefin containing no by-products can be efficiently obtained with an inexpensive and compact facility.

BRIEF DESCRIPTION OF DRAWINGS

FIG. 1 is a schematic flow chart illustrating an example of the process for performing the present invention.

DESCRIPTION OF EMBODIMENTS

The present invention is a method for producing an α-olefin, including a step 1 of continuously introducing an ethylene and a catalyst into a reactor, followed by performing a polymerization reaction to obtain a reaction mixture, and a step 2 of continuously introducing the reaction mixture and a base into a line mixer, followed by performing mixing, in which the line mixer has a stirring power of 30 to 1000 $kW \cdot sec/m^3$ and a number of passes of 5 to 50.

Each of the steps of the present invention is described below.

[Step 1]

The step 1 is a step of continuously introducing an ethylene and a catalyst into a reactor, followed by performing a polymerization reaction to obtain a reaction mixture. In the present step, ethylene is subjected to a polymerization reaction and a reaction mixture containing α-olefin is obtained.

<Catalyst>

In the step 1, catalyst is used to polymerize ethylene. As the catalyst, a Ziegler-based catalyst is preferred. In the case of using catalyst containing a halogen atom that is chlorine atom, bromine atom, or iodine atom, the effect of the present invention is exerted.

The Ziegler-based catalyst preferably contains a combination of (A) a transition metal compound and (B) an organoaluminum, and, in addition, (C) a third component to be used as desired.

Among these, compounds containing a halogen atom, especially chlorides are simple in structure thereof, excellent in availability, and inexpensive, and therefore suitable for industrial production. They are also excellent in performance as catalyst. According to the production method of the present invention, also in the case of using such a catalyst, α-olefin containing no organohalogen compounds can be efficiently obtained with an inexpensive and compact facility.

As the (A) transition metal compound, a compound represented by the general formula (I) may be used:

$$MX_xY_yO_z \tag{I}$$

in which M represents a zirconium atom or a titanium atom; X represents a chlorine atom, a bromine atom, or an iodine atom; Y represents RO—, $R_2N$—, —OCOR, —$OSO_3R$, R—, —Cp, or a β-diketonato represented by the formula (II), in which —Cp represents a cyclopentadienyl group and R represents a linear or branched alkyl group having 1 to 20 carbon atoms:

(II)

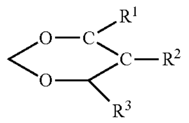

in which $R^1$, $R^2$, and $R^3$ each independently represent a hydrogen atom, an alkyl group having 1 to 20 carbon atoms, or an alkyl group which is substituted with a halogen atom and which has 1 to 20 carbon atoms, with the proviso that at least one of $R^1$, $R^2$, and $R^3$ is an alkyl group which is substituted with a halogen atom and which has 1 to 20 carbon atoms; and x, y, and z each independently represent an integer of 0 to 4, with the proviso that x+y+z=4.

M is preferably a zirconium atom. X is preferably a chlorine atom. x is preferably 4. y is preferably 0. z is preferably 0.

Specific examples of such a compound include $ZrCl_4$, $ZrBr_4$, $ZrI_4$, $ZrBrCl_3$, $ZrBr_2Cl_2$, $TiCl_4$, $TiBr_4$, $TiI_4$, $TiBrCl_3$, $TiBr_2Cl_2$, $Zr(OC_2H_5)_4$, $Zr(OC_2H_5)_2Cl_2$, $Zr(O\text{-}n\text{-}C_3H_7)_4$, $Zr(O\text{-}n\text{-}C_3H_7)_2Cl_2$, $Zr(O\text{-}iso\text{-}C_3H_7)_4$, $Zr(O\text{-}iso\text{-}C_3H_7)_2Cl_2$, $Zr(O\text{-}n\text{-}C_4H_9)_4$, $Zr(O\text{-}n\text{-}C_4H_9)_2Cl_2$, $Zr(O\text{-}iso\text{-}CH_9)_4$, $Zr(O\text{-}iso\text{-}C_4H_9)_2Cl_2$, $Zr(O\text{-}tert\text{-}C_4H_9)_4$, $Zr(O\text{-}tert\text{-}C_4H_9)_2Cl_2$, $Zr((CH_3)_2N)_4$, $Zr((C_2H_5)_2N)_4$, $Zr((n\text{-}C_3H_7)_2N)_4$, $Zr((iso\text{-}C_3H_7)_2N)_4$, $Zr((n\text{-}C_4H_9)_2N)_4$, $Zr((tert\text{-}C_4H_9)_2N)_4$, $Zr(OSO_3CH_3)_4$, $Zr(OSO_3C_2H_5)_4$, $Zr(OSO_3C_3H_7)_4$, $Zr(OSO_3C_4H_9)_4$, $ZrCp_2Cl_2$, $ZrCp_2ClBr$, $Ti(OC_2H_5)_4$, $Ti(OC_2H_5)_2Cl_2$, $Ti(O\text{-}n\text{-}C_3H_7)_4$, $Ti(O\text{-}n\text{-}C_3H_7)_2Cl_2$, $Ti(O\text{-}iso\text{-}C_3H_7)_4$, $Ti(O\text{-}iso\text{-}C_3H_7)_2Cl_2$, $Ti(O\text{-}n\text{-}C_4H_9)_4$, $Ti(O\text{-}n\text{-}C_4H_9)_2Cl_2$, $Ti(O\text{-}iso\text{-}C_4H_9)_4$, $Ti(O\text{-}iso\text{-}C_4H_9)_2Cl_2$, $Ti(O\text{-}tert\text{-}C_4H_9)_4$, $Ti(O\text{-}tert\text{-}C_4H_9)_2Cl_2$, $Ti((CH_3)_2N)_4$, $Ti((C_2H_5)_2N)_4$, $Ti((n\text{-}C_3H_7)_2N)_4$, $Ti((iso\text{-}C_3H_7)_2N)_4$, $Ti((n\text{-}C_4H_9)_2N)_4$, $Ti((tert\text{-}C_4H_9)_2N)_4$, $Ti(OSO_3CH_3)_4$, $Ti(OSO_3C_2H_5)_4$, $Ti(OSO_3C_3H_7)_4$, $Ti(OSO_3C_4H_9)_4$, $TiCp_2Cl_2$, $TiCp_2ClBr$, $Zr(OCOC_2H_5)_4$, $Zr(OCOC_2H_5)_2Cl_2$, $Zr(OCOC_3H_7)_4$, $Zr(OCOC_3H_7)_2Cl_2$, $Zr(OCOCH_9)_4$, $Zr(OCOC_4H_9)_2Cl_2$, $Ti(OCOC_2H_5)_4$, $Ti(OCOC_2H_5)_2Cl_2$, $Ti(OCOC_3H_7)_4$, $Ti(OCOC_3H_7)_2Cl_2$, $Ti(OCOC_4H_9)_4$, $Ti(OCOCH_9)_2Cl_2$, $ZrCl_2(HCOCFCOF)_2$, and $ZrCl_2(CH_3COCFCOCH_3)_2$. Among these, $ZrCl_4$, $Zr(O\text{-}n\text{-}C_3H_7)_4$, and $Zr(O\text{-}n\text{-}C_4H_9)_4$ are preferred, and $ZrCl_4$ is more preferred.

Examples of the (B) organoaluminum include a compound represented by the general formula (III) and/or the general formula (IV):

$$AlY_aX_bO_cN_d \tag{III}$$

in which X represents a chlorine atom, a bromine atom, or an iodine atom; Y represents RO—, $R_2N$—, —OCOR, or R—, where R represents a linear or branched alkyl group having 1 to 20 carbon atoms; and a, b, c, and d each independently represent an integer of 0 to 3, with the proviso that a+b+c+d=3.

$$Al_2Y_{a'}X_{b'}O_{c'}N_{d'} \quad (IV)$$

In the formula, X represents a chlorine atom, a bromine atom, or an iodine atom; Y represents RO—, $R_2N$—, —OCOR, —RCOCR'COR", or R—, where R, R' and R" each independently represent a linear or branched alkyl group having 1 to 20 carbon atoms; and a', b', c', and d' each independently represent an integer of 0 to 6, with the proviso that a'+b'+c'+d'=6.

Examples of the compound represented by the general formula (III) include $Al(CH_3)_3$, $Al(C_2H_5)_3$, $Al(C_3H_7)_3$, Al(iso-$C_3H_7)_3$, $Al(C_4H_9)_3$, Al(iso-$C_4H_9)_3$, $Al(C_5H_{11})_3$, $Al(C_6H_{13})_3$, $Al(C_8H_{17})_3$, $Al(C_2H_5)_2Cl$, $Al(C_2H_5)_2Br$, $Al(C_2H_5)_2I$, $Al(C_2H_5)Cl_2$, $Al(C_2H_5)Br_2$, $Al(C_2H_5)_{12}$, $AlC_2H_5(OC_2H_5)_2$, $AlC_2H_5(OC_3H_7)_2$, $AlC_2H_5(OCH_9)_2$, $Al(OC_2H_5)_2Cl$, $Al(OC_3H_7)_2Cl$, $Al(OC_4H_9)_2Cl$, $Al(OC_2H_5)Cl_2$, $Al(OC_3H_7)Cl_2$, $Al(OCH_9)Cl_2$, $AlC_2H_5(OCOC_2H_5)_2$, $AlC_2H_5(OCOC_3H_7)_2$, $AlC_2H_5(OCOCH_9)_2$, $Al(OCOC_2H_5)_2Cl$, $Al(OCOC_3H_7)_2Cl$, and, $Al(OCOC_4H_9)_2Cl$, $Al(OCOC_2H_5)Cl_2$, $Al(OCOC_3H_7)Cl_2$, $Al(OCOCH_9)Cl_2$, $Al(C_2H_5)_2OC_2H_5$, $Al(C_2H_5)_2OC_3H_7$, $Al(C_2H_5)_2OCH_9$, $Al(C_2H_5)_2(N(C_2H_5)_2)$, $Al(C_2H_5)_2(N(C_3H_7)_2)$, and $Al(C_2H_5)_2N(C_4H_9)_2$. Among these, $Al(C_2H_5)_3$, Al(iso-$C_4H_9)_3$, and $Al(C_8H_{17})_3$ are preferred, and $Al(C_2H_5)_3$ is more preferred.

Examples of the compound represented by the general formula (IV) include $Al_2(CH_3)_3Cl_3$, $Al_2(CH_3)_3Br_3$, $Al_2(C_2H_5)_3Cl_3$, $Al_2(C_2H_5)_3Br_3$, $Al_2(C_2H_5)_3Cl_3$, $Al_2(C_2H_5)_3BrCl_2$, $Al_2(C_3H_7)_3Cl_3$, $Al_2$(iso-$C_3H_7)_3Cl_3$, $Al_2(C_4H_9)_3Cl_3$, $Al_2$(iso-$C_4H_9)_3Cl_3$, $Al_2(C_5H_{11})_3Cl_3$, $Al_2(C_8H_{17})_3Cl_3$, $Al_2(C_2H_5)_2(CH_3)Cl_3$, $Al_2(OC_2H_5)_3Cl_3$, $Al_2(OC_3H_7)_3Cl_3$, $Al_2(OCH_9)_3Cl_3$, $Al_2(OCOC_2H_5)_3Cl_3$, $Al_2(OCOC_3H_7)_3Cl_3$, and $Al_2(OCOC_4H_9)_3Cl_3$. Among these, $Al_2(CH_3)_3Cl_3$, $Al_2(C_2H_5)_3Cl_3$, and $Al_2$(iso-$C_4H_9)_3Cl_3$ are preferred, and $Al_2(C_2H_5)_3Cl_3$ is more preferred.

As the third component (C), which is used as desired, at least one compound selected from the group consisting of a sulfur compound, a phosphorus compound, and a nitrogen compound may be used. The third component contributes to improvement of the purity of the α-olefin to be obtained.

The sulfur compound is not limited as long as it is an organosulfur compound, and preferred examples of the sulfur compound include thioethers such as dimethyl sulfide, diethyl sulfide, dipropyl sulfide, dihexyl sulfide, dicyclohexyl sulfide, and diphenyl thioether; dialkyl disulfide compounds such as dimethyl disulfide, diethyl disulfide, dipropyl disulfide, dibutyl disulfide, dihexyl disulfide, dicyclohexyl disulfide, and ethylmethyl disulfide; thiophenes such as thiophene, 2-methylthiophene, 3-methylthiophene, 2,3-dimethylthiophene, 2-ethylthiophene, and benzothiophene, and heterocyclic sulfur compounds such as tetrahydrothiophene and thiopyrane; aromatic sulfur compounds such as diphenyl sulfide, diphenyl disulfide, methylphenyl disulfide, and methylphenyl sulfide; thiourea; and sulfides such as methyl sulfide, ethyl sulfide, and butyl sulfide.

The phosphorus compound is not limited as long as it is an organophosphorus compound, and preferred examples of the phosphorus compound include phosphines such as triphenylphosphine, triethylphosphine, tributylphosphine, tripropylphosphine, trioctylphosphine, and tricyclohexylphosphine. The nitrogen compound is not limited as long as it is an organonitrogen compound, and preferred examples of the nitrogen compound include organic amines such as methylamine, ethylamine, propylamine, butylamine, pentylamine, hexylamine, cyclohexylamine, octylamine, decylamine, aniline, benzylamine, naphthylamine, dimethylamine, diethylamine, dibutylamine, diphenylamine, methylphenylamine, trimethylamine, triethylamine, tributylamine, triphenylamine, pyridine, and picoline.

Among the sulfur compounds, phosphorus compounds, and nitrogen compounds, for example, one or two or more compounds selected from the group consisting of dimethyl disulfide, thiophene, thiourea, triphenylphosphine, tributylphosphine, trioctylphosphine, and aniline may be preferably used.

<Conditions, Etc. of Polymerization Reaction>

The polymerization reaction of ethylene is preferably performed in an organic solvent. The amount of the organic solvent used in the polymerization reaction of ethylene is preferably 0.5 times to 5 times (by mass rate) of α-olefin to be produced. Examples of the organic solvent include alicyclic compounds such as cyclohexane and decalin; aromatic hydrocarbons such as benzene, toluene, xylene, chlorobenzene, ethylbenzene, dichlorobenzene, and chlorotoluene, and halides thereof; aliphatic hydrocarbons such as pentane, hexane, heptane, octane, nonane, and decane; and halogenated aliphatic hydrocarbons such as dichloroethane and dichlorobutane. Among these, alicyclic compounds are preferred, and cyclohexane is more preferred.

In the present step, regarding the blending ratio of the (A) transition metal compound relative to the organic solvent in the catalyst, the amount of the (A) transition metal compound is preferably 0.01 to 5 mmol and more preferably 0.03 to 1 mmol relative to 250 ml of the organic solvent. Regarding the blending ratio of the (B) organoaluminum relative to the organic solvent in the catalyst, the amount of the (B) organoaluminum is preferably 0.05 to 15 mmol and more preferably 0.06 to 3 mmol relative to 250 mL of the organic solvent. Regarding the blending ratio of the (C) third component relative to the organic solvent in the catalyst, relative to 250 mL of the organic solvent, the amount of the (C) third component is preferably 0.05 to 20 mmol; in the case where the sulfur compound is used as the (C) third component, the amount is preferably 0.1 to 10 mmol; in the case where the nitrogen compound or the phosphorus compound is used as the (C) third component, the amount is preferably 0.05 to 5 mmol. With respect to the blending ratio between the (A) transition metal compound and the (B) organoaluminum, Al/Zr or Ti (molar ratio) is preferably set to fall within the range of 1 to 15. The blending ratio [Al/Zr or Ti (molar ratio)] between the (A) transition metal compound and the (B) organoaluminum is more preferably 2 to 10 and further preferably 4 to 9.

The polymerization reaction in the present step is performed preferably at a temperature of 100 to 150° C. under a pressure of 30 to 90 $kg/cm^2 \cdot G$ (2.94 to 8.82 MPa). Ethylene gas pressure is preferably 30 to 90 $kg/cm^2 \cdot G$ (2.94 to 8.82 MPa) and more preferably 50 to 80 $kg/cm^2 \cdot G$ (4.90 to 7.84 MPa). While the reaction time varies depending on the temperature and pressure and cannot be specified in a uniform manner, it is preferably 10 minutes or more and more preferably 30 minutes or more, and preferably 60 minutes or less and more preferably 50 minutes or less. In the case of using a continuous reaction device, a residence time in the reaction device is preferably 10 minutes or more and more preferably 30 minutes or more, and preferably 60 minutes or less and more preferably 50 minutes or less. The reactor is preferably a complete mixing tank-type reactor.

The reaction mixture after the polymerization reaction normally contains unreacted ethylene in addition to α-olefin as the reaction product. Before the succeeding step 2, ethylene and α-olefin may be separated from the reaction mixture to recover unreacted ethylene. Namely, there may be provided a separation step of separating a reaction mixture containing unreacted ethylene and α-olefin from the reaction mixture after the polymerization reaction to recover the unreacted ethylene. In the case of providing the separation step, the reaction mixture containing α-olefin after the separation is subjected to the step 2. For the separation step, a flasher is preferably used. FIG. 1 illustrates a flasher 15 as an example of a device for recovering unreacted ethylene. In the flasher 15, unreacted ethylene 16 is recovered from an upper part of the flasher.

The unreacted ethylene separated and recovered may be recycled and used in the polymerization reaction in the step 1. The unreacted ethylene recycled and used in the polymerization reaction in the step 1 contains α-olefin that has not been completely separated in the separation step. When such an α-olefin is reused in the polymerization reaction, it induces a side reaction in the polymerization reaction to produce by-products such as α-olefins having a branched structure. Therefore, it is preferred to perform purification in a distillation column or the like so that a content of α-olefin in unreacted ethylene to be recycled in the polymerization reaction is 2% by mass or less.

In the step 2, the reaction mixture after the polymerization reaction may be used as it is, or the reaction mixture obtained by removing unreacted ethylene from the reaction mixture after the polymerization reaction in accordance with the above-described method may be used.

[Step 2]

The step 2 is a step of continuously introducing the reaction mixture obtained in the step 1 and a base into a line mixer, followed by performing mixing, in which in the mixing, a stirring power is 30 to 1000 kW·sec/m$^3$ and a number of passes is 5 to 50.

By mixing the reaction mixture and a base, the catalyst is deactivated. Namely, the step 2 is a step of continuously introducing the reaction mixture obtained in the step 1 and a base into a line mixer, followed by performing mixing, to deactivate the catalyst, in which in the mixing, a stirring power is 30 to 1000 kW·sec/m$^3$ and a number of passes is 5 to 50.

In FIG. 1, the reaction mixture obtained in a reactor 1, which contains catalyst, solvent, and α-olefin, is continuously introduced into a line mixer 5 via a control valve 2 and further through a junction 6 and an inlet 7 of the line mixer. Before the reaction mixture is supplied to the line mixer 5, a device such as the flasher 15 may be provided in order to recover unreacted ethylene contained in the reaction mixture. The base (preferably ammonia) as a deactivating agent is, in the form of aqueous solution, continuously introduced into the line mixer 5 from a deactivating agent tank (ammonia water tank) 3, via a pump 4, and further through the junction 6 and the inlet 7 of the line mixer.

The reaction mixture and the base introduced into the line mixer 5 are mixed to deactivate the catalyst contained in the reaction mixture.

The line mixer is preferably one with a turbine (rotor) and a stator, and more preferably one that performs mixing by shear force in a gap between the turbine (rotor) and the stator. By using such a line mixer, the base and the catalyst can be mixed and brought into contact with each other at high speed with a small device.

As the line mixer, a commercially available line mixer can be used. Examples of the commercially available line mixer include Pipeline-Homo Mixer manufactured by PRIMIX Corporation.

In the present step, the line mixer has a stirring power of preferably 30 to 1000 kW·sec/m$^3$, more preferably 50 to 500 kW·sec/m$^3$, and further preferably 100 to 300 kW·sec/m$^3$. From a viewpoint of a sufficient mixing, 30 kW·sec/m$^3$ or more is preferred. From a viewpoint of inhibiting mechanical load and heat generation, 1000 kW·sec/m$^3$ or less is preferred. From the viewpoint of a sufficient mixing, 150 to 300 kW·sec/m$^3$ is furthermore preferred. Meanwhile, from the viewpoint of inhibiting mechanical load and heat generation, 100 to 150 kW·sec/m$^3$ is furthermore preferred. In the case that the reaction mixture and the base to be mixed contain organic solvent and water, oil-water separation after the mixing can be made easier by setting the stirring power to be 1000 kW·sec/m$^3$ or less.

A number of passes is preferably 5 to 50, more preferably 5 to 30, and further preferably 5 to 20. From a viewpoint of sufficiently imparting shear force to mix, 5 or more is preferred. From a viewpoint of inhibiting mechanical load and heat generation, 50 or less is preferred.

By employing the above-described stirring power and number of passes, time required for the catalyst deactivation can be shortened while sufficiently deactivating the catalyst. Namely, by mixing the reaction mixture and the base using the line mixer with the stirring power and number of passes of the above-described conditions, deactivation of the catalyst can be performed efficiently, and a side reaction can be inhibited to suppress the production of organohalogen compounds.

The stirring power in the present description means power applied per unit amount of treatment solution (mixture of the reaction mixture and the base) and is calculated from the formula (1) based on power (P) [kW] in a stirring space and volume flow (Q) [m$^3$/sec].

$$\text{Stirring power} = P/Q\ [\text{kW}\cdot\text{sec}/m^3] \qquad \text{Formula (1)}$$

The number of passes in the present description means an average number of shearing times which treatment fluid (mixture of the reaction mixture and the base) undergoes while passing through the line mixer and is calculated from the formula (2) based on number of rotations (n) [1/sec] and a wing diameter (d) [m] of the line mixer, and the volume flow Q [m$^3$/sec].

$$\text{Number of passes} = n\cdot d^3/Q \qquad \text{Formula (2)}$$

In the case of installing plural line mixers in series, or in the case that one line mixer has plural stirring units in series, the stirring power in the present embodiment means the total value of each of the stirring powers of the plural constitutions, and the number of passes means the total value of each of the numbers of passes of the plural constitutions. The number of the constitutions (the product of the number of line mixers installed in series and the number of stirring units installed in series in one line mixer) is preferably 4 or less, more preferably 3 or less, more preferably 2 or less, and further preferably 1. In the case of employing the constitutions in parallel, the stirring power and the number of passes in the present embodiment mean a value of each single constitution.

In the production of α-olefin, it is considered that, since the base and the catalyst can be mixed at high speed by using the line mixer as a mixer for deactivating the catalyst, a side reaction that occurs by the contact of water and the catalyst can be inhibited, and therefore the production of organohalogen compounds produced by the side reaction can be inhibited.

Further in the present invention, it is considered that, by adjusting not only the power but also the number of shearing times in using the line mixer, the reaction can be controlled while making fluid to pass continuously. Thus, it is considered that, by using the line mixer as a mixer for deactivating the catalyst and also by setting the stirring power and the number of passes to fall within the above-described ranges, α-olefin can be efficiently produced while continuously and sufficiently deactivating the catalyst and inhibiting the production of organohalogen compounds.

In the present step, the reaction mixture and the base are continuously introduced into the line mixer, followed by performing mixing, and those are brought into contact with each other before being introduced into the line mixer. Namely, the present production method preferably includes a step of bringing the reaction mixture into contact with the base before continuously introducing the reaction mixture and the base into the line mixer.

In addition, a distance between a junction at which the reaction mixture contacts the base and an inlet of the line mixer is preferably 1 m or less.

A specific description is given below with reference to FIG. 1.

In FIG. 1, the reaction mixture and the base are brought into contact with each other at the junction 6, pass the inlet 7 of the line mixer, and are introduced into the line mixer 5. Here, the distance between the junction 6 at which the reaction mixture contacts the base and the inlet 7 of the line mixer is preferably 1 m or less, more preferably 50 cm or less, and further preferably 20 cm or less. When the distance between the junction at which the reaction mixture contacts the base and the inlet of the line mixer falls within the above ranges, since the mixing of the base and the reaction mixture can be performed quickly to deactivate the catalyst in the reaction mixture, a side reaction that occurs by the contact of the catalyst and water that can be contained in the base can be inhibited, and therefore the by-production of organohalogen compounds produced by the side reaction can be inhibited.

The mixture mixed in the line mixer 5 is discharged from the line mixer, and then sent to a deasher 8 to be subjected to a deashing step.

The base in the present step is preferably at least one selected from the group consisting of ammonia, amines, and alkali metal hydroxides, more preferably at least one selected from the group consisting of ammonia and amines, and further preferably ammonia.

Examples of the amines include methylamine, ethylamine, propylamine, butylamine, pentylamine, hexylamine, cyclohexylamine, octylamine, decylamine, aniline, benzylamine, naphthylamine, dimethylamine, diethylamine, dibutylamine, diphenylamine, methylphenylamine, trimethylamine, triethylamine, tributylamine, triphenylamine, pyridine, and picoline.

Examples of the alkali metal hydroxides include sodium hydroxide and potassium hydroxide.

Ammonia and amines are easy to be dissolved in an organic phase, and can quickly contact the catalyst to deactivate it. Among these, ammonia has a small molecular weight, and therefore can efficiently perform deactivation with a small amount.

It is further preferred to use ammonia or the amines and the alkali metal hydroxides in combination. The alkali metal hydroxides are strong bases and have an effect of increasing pH of a water phase, and therefore have an effect of making it easier to dissolve an aluminum salt produced by the deactivation of the catalyst in the water phase.

A used amount of the base is, relative to the content of halogen in the catalyst, preferably 30 times by mol or more and more preferably 50 times by mol or more. Upper limit is not limited, but the used amount is preferably 150 times by mol or less relative to the content of halogen in the catalyst.

These bases are preferably used in the form of aqueous solution. The aqueous solution has a base concentration of preferably 1 to 30% by mass and more preferably 10 to 30% by mass. When the concentration of the aqueous solution falls within the above-described ranges, by-production of organohalogen compounds can be more reduced.

A mixing ratio [solvent; aqueous solution containing base] between the solvent contained in the reaction mixture and the aqueous solution containing the base in mixing the reaction mixture and the base in the line mixer is preferably 1:10 to 100:1 (mass ratio), more preferably 1:1 to 100:1 (mass ratio), and more preferably 5:1 to 20:1 (mass ratio).

A temperature in mixing (temperature of liquid in the line mixer) is preferably 90 to 150° C. and more preferably 100 to 130° C.

A pressure in mixing is preferably a pressure at which no gas is generated in the line mixer. The pressure in mixing is preferably 0.5 to 2.0 MPa (G) and more preferably 0.9 to 1.5 MPa (G).

[Step 3 and Step 4]

The production method of the present invention preferably further includes, after the step 2, a deashing step 3 of removing the deactivated catalyst, and a distillation step 4 of recovering the α-olefin.

A specific description is given below with reference to FIG. 1.

The mixture mixed in the step 2 is discharged from the line mixer 5, and then sent to the deasher 8 to be subjected to the deashing step. In the deashing step, by adding water 9 to the mixture, followed by stirring, the deactivated catalyst is dissolved in the water and the catalyst is removed from the mixture. Thereafter, the water containing the deactivated catalyst is separated in an oil-water separation tank 10 and the water containing the deactivated catalyst is discarded as waste water 11 to the outside of the system.

An amount of the water added in the deashing step is preferably 1/10 to 1/3 (mass ratio) of an oil phase (the above-described mixture).

A temperature in stirring is preferably 90° C. to 150° C.

The mixture having gone through the deashing step is sent to a distillation system and subjected to the distillation step 4. In the distillation system, in the case that the mixture contains organic solvent, the solvent is removed and the α-olefin as the objective product is recovered.

An example of the distillation column is illustrated in FIG. 1. The mixture having gone through the deashing step is introduced to a distillation column 12, and liquid 13 mainly containing α-olefins having low molecular weights is obtained from a column top and liquid 14 mainly containing α-olefins having high molecular weights and solvent is obtained from a column bottom. By performing fractionation of the liquids as necessary, α-olefin having an appropriate number of carbons (degree of polymerization) for the application can be obtained.

A halogen content of the obtained α-olefin is preferably 2 ppm by mass or less, more preferably 1 ppm by mass or less, and further preferably 0.5 ppm by mass or less. When the halogen content is 2 ppm by mass or less, in the case of using the α-olefin as a monomer or a comonomer of various polyolefins, there is preferably no adverse effect on catalyst used for a reaction between the α-olefin and other starting materials.

The halogen content of the α-olefin reflects an amount of organohalogen compounds contained in the α-olefin, and when the halogen content of the α-olefin is small, it can be said that the amount of organohalogen compounds contained in the α-olefin is also small.

EXAMPLES

The present invention is described below in more detail by way of Examples, but the present invention is not limited by the Examples.

Example 1

[Preparation of Catalyst]

Catalyst was prepared according to the following procedure. Dry cyclohexane was introduced to a stirring tank having an internal volume of 6.5 $m^3$ under nitrogen atmosphere. Next, triethylaluminum [$(C_2H_5)_3Al$] was introduced. Zirconium tetrachloride anhydride [$ZrCl_4$] was further introduced. Then, ethylaluminum sesquichloride [$(C_2H_5)_3Al_2Cl_3$] was introduced.

Amounts of the above-described starting materials and solvent introduced were based on the amount of zirconium tetrachloride anhydride as follows. Triethylaluminum and ethylaluminum sesquichloride were introduced such that $(C_2H_5)_3Al_2Cl_3/(C_2H_5)_3Al=3.5$ (molar ratio) and $[(C_2H_5)_3Al_2Cl_3+(C_2H_5)_3Al]/ZrCl_4=7$ (molar ratio) were satisfied. Cyclohexane was introduced such that the concentration of zirconium tetrachloride anhydride was 80 mmol relative to 1 L of cyclohexane.

After the addition of all components, the resulting mixture was heated at 70° C. with stirring for 2 hours under nitrogen atmosphere to allow complex formation, thereby preparing a catalyst liquid.

[Step 1: Polymerization Reaction]

The reaction was continuously performed using a complete mixing tank-type reactor (internal volume: about 20 $m^3$) (FIG. 1: reactor 1). Reaction solvent (cyclohexane) was fed at a rate of 30 tons/hour and the catalyst liquid was fed at a rate of 25 kg/hour. An average residence time was set to about 45 minutes based on the solvent. The reaction was performed at 130° C. at 70 kg/$cm^2$·G (6.9 MPa) with stirring at 70 rpm. High-purity ethylene gas was continuously supplied such that a reaction pressure of 70 kg/$cm^2$·G was maintained.

A liquid reaction product containing a polymerization reaction product (α-olefin) obtained in the polymerization reaction was introduced into a flasher (FIG. 1: flasher 15) and gas-liquid separation was performed to obtain a gas component containing unreacted ethylene and a reaction mixture that is a liquid component containing the reaction product. The reaction mixture was used in the step 2.

[Step 2: Deactivation Step]

The reaction mixture obtained in the step 1 and ammonia water having a concentration of 20% by mass were continuously supplied to a line mixer (trade name: Pipeline-Homo Mixer manufactured by PRIMIX Corporation) (FIG. 1: line mixer 5) so that a mass ratio of reaction solvent contained in the reaction mixture: ammonia water=10:1 was satisfied, and deactivation of the catalyst was performed under conditions of a stirring power being 201 kW·sec/$m^3$, a number of passes being 6.9, and a temperature being 110° C. A flow rate in a pipe line from the contact between the reaction mixture and the ammonia water to the introduction into the line mixer was about 1.2 m/sec, and a distance (the distance in FIG. 1 from the junction 6 to the inlet 7 of the line mixer) from the contact to the introduction into the line mixer was 15 cm.

[Step 3: Deashing Step]

The mixture liquid discharged from the line mixer was sent to a deasher (orifice mixer) (FIG. 1: deasher 8), water was added thereto so that a mass ratio of reaction solvent: water=3:1 was satisfied, and deashing was performed at 110° C. The obtained mixture liquid was sent to an oil-water separation tank (FIG. 1: oil-water separation tank 10), and an oil phase was sent to a distillation system.

[Step 4: Distillation Step]

By adjusting distillation conditions appropriately in a distillation unit (FIG. 1: distillation column 12 or the like), α-olefins each having 4 to 24 carbon atoms were recovered.

Average halogen contents of each of the obtained α-olefins were 0.5 ppm by mass or less.

Example 2

α-Olefins having various numbers of carbon atoms were produced in the same manner as in Example 1, except for setting the stirring power to be 141 kW·sec/$m^3$ and the number of passes to be 6.1. Average halogen contents of each of the obtained α-olefins were 0.5 ppm by mass or less.

Comparative Example 1

α-Olefins having various numbers of carbon atoms are produced in the same manner as in Example 1, except for setting the stirring power to be 46 kW·sec/$m^3$ and the number of passes to be 4.2. Average halogen contents of each of the obtained α-olefins are 3 ppm by mass or more, since the reaction mixture and the base are not sufficiently mixed.

Comparative Example 2

α-Olefins having various numbers of carbon atoms are produced in the same manner as in Example 1, except for setting the stirring power to be 3 kW·sec/$m^3$ and the number of passes to be 1.7. Average halogen contents of each of the obtained α-olefins are 3 ppm by mass or more, since the reaction mixture and the base are not sufficiently mixed.

REFERENCE SIGNS LIST

- 1: Reactor
- 2: Control valve
- 3: Deactivating agent tank (ammonia water tank)
- 4: Pump
- 5: Line mixer
- 6: Junction
- 7: Inlet of line mixer
- 8: Deasher

10: Oil-water separation tank

12: Distillation column

15: Flasher

The invention claimed is:

1. A method for producing an α-olefin, the method comprising:

(1) continuously introducing an ethylene and a catalyst into a reactor, followed by performing a polymerization reaction to obtain a reaction mixture; and (2) continuously introducing the reaction mixture and a base into a line mixer, followed by performing mixing, wherein the line mixer has a stirring power in a range of from 30 to 1000 kW·sec/$m^3$ and a number of passes in a range of from 5 to 50.

2. The method of claim 1, further comprising:

bringing the reaction mixture into contact with the base before continuously introducing the reaction mixture and the base into the line mixer, wherein a distance between a junction at which the reaction mixture contacts the base and an inlet of the line mixer is 1 m or less.

3. The method of claim 1, wherein the catalyst is a Ziegler-based catalyst.

4. The method of claim 1, wherein the base is an ammonia.

5. The method of claim 1, further comprising, after the step-continuously introducing (2);

(3) deashing comprising removing the deactivated catalyst; and (4) distilling for recovering the α-olefin.

* * * * *